US006829326B2

(12) United States Patent
Woods et al.

(10) Patent No.: US 6,829,326 B2
(45) Date of Patent: Dec. 7, 2004

(54) METHOD FOR IMAGING THE HEAD AREA

(75) Inventors: Douglas Woods, Franklin, WI (US); Panu Kopsala, Tuusula (FI)

(73) Assignee: Instrumentarium Corp., Helsinki (FI)

( * ) Notice: Subject to any disclaimer, the term of this patent is extended or adjusted under 35 U.S.C. 154(b) by 234 days.

(21) Appl. No.: 10/204,106

(22) PCT Filed: Feb. 14, 2001

(86) PCT No.: PCT/FI01/00136

§ 371 (c)(1),
(2), (4) Date: Oct. 10, 2002

(87) PCT Pub. No.: WO01/60256

PCT Pub. Date: Aug. 23, 2001

(65) Prior Publication Data

US 2003/0161438 A1 Aug. 28, 2003

(30) Foreign Application Priority Data

Feb. 18, 2000 (FI) .............................................. 20000368

(51) Int. Cl.[7] ................................................. A61B 6/14
(52) U.S. Cl. ........................................ 378/38; 378/196
(58) Field of Search ...................... 378/38–40, 195–196

(56) References Cited

U.S. PATENT DOCUMENTS

| 4,783,793 A | 11/1988 | Virta et al. |
| 5,058,147 A | 10/1991 | Nishikawa et al. |
| 5,454,023 A | 9/1995 | Asikainen |
| 5,511,106 A | 4/1996 | Doebert et al. |
| 5,692,027 A | * 11/1997 | Yoshimura et al. ........... 378/38 |
| 6,466,641 B1 | * 10/2002 | Virta et al. ................... 378/38 |
| 6,731,717 B2 | * 5/2004 | Kopsala ....................... 378/38 |

FOREIGN PATENT DOCUMENTS

DE    19735112    2/1999

* cited by examiner

Primary Examiner—Craig E. Church
(74) Attorney, Agent, or Firm—Andrus, Sceales, Starke & Sawall, LLP

(57) ABSTRACT

The invention relates to a method for imaging the head area by using a line detector camera (8) equipped with a digital detector, at which camera is directed an X-ray beam (11) through the object being imaged. In the method is used an apparatus (1) which makes possible the implementation of cephalometric imaging and at least one other imaging method, such as panoramic imaging. The apparatus comprises an X-ray source (5), a primary collimator (6) in conjunction with the X-ray source, a line detector camera (8), which is located to a position further away from the X-ray source (5) for implementing cephalometric imaging and/or to a position closer to the said X-ray source for the said other imaging method, and a secondary collimator (9) in the vicinity of the line detector camera (8) intended for cephalometric imaging. In the method, the radiation emitted from the X-ray source (5) is collimated in cephalometric imaging without turning the X-ray source in such a way that the ray beam (11) bypasses the position of the line detector camera (8) closer to the X-ray source (5).

5 Claims, 3 Drawing Sheets

METHOD FOR IMAGING THE HEAD AREA

CROSS REFERENCE TO RELATED APPLICATION

The present application is the U.S. national stage application of International Application PCT/FI01/00136, filed Feb. 14, 2001, which international application was published on Aug. 23, 2001 as International Publication WO 01/60256. The International Application claims priority of Finnish Patent Application 20000368, filed Feb. 18, 2000.

SUMMARY OF THE INVENTION

The present invention relates to a method for imaging the head area by using a line detector camera equipped with a digital detector, at which line detector camera is directed an X-ray beam through the object being imaged, in which method is used an apparatus which makes possible the implementation of cephalometric imaging and at least one other imaging method, such as panoramic imaging, which apparatus comprises an X-ray source, a primary collimator in conjunction with the X-ray source, a line detector camera, which is located to a position further away from the X-ray source for cephalometric imaging and/or to a position closer to the X-ray source for the said other imaging method, and a secondary collimator in the vicinity of the line detector camera intended for cephalometric imaging.

BRIEF DESCRIPTION OF THE INVENTION

One object of the present invention is to provide a simple method by means of which the same apparatus can be used for carrying out at least two different types of imaging methods, for example, cephalometric imaging and panoramic imaging, through simple procedures. To achieve this object, the method relating to the invention is characterised in that in the method, the radiation emitted from the X-ray source is collimated in cephalometric imaging in such a way that the ray beam bypasses the position of the line detector camera closer to the X-ray source.

According to the method relating to the invention is achieved a solution by means of which the imaging apparatus is made easily extendable, wherein either one joint line detector camera, or separate cameras for different types of imaging, can be used. This makes possible free configuration of the apparatus.

BRIEF DESCRIPTION OF THE DRAWING

The invention is described in greater detail in the following, with reference to the accompanying drawings, in which.

DETAILED DESCRIPTION OF THE INVENTION

Figure 1:
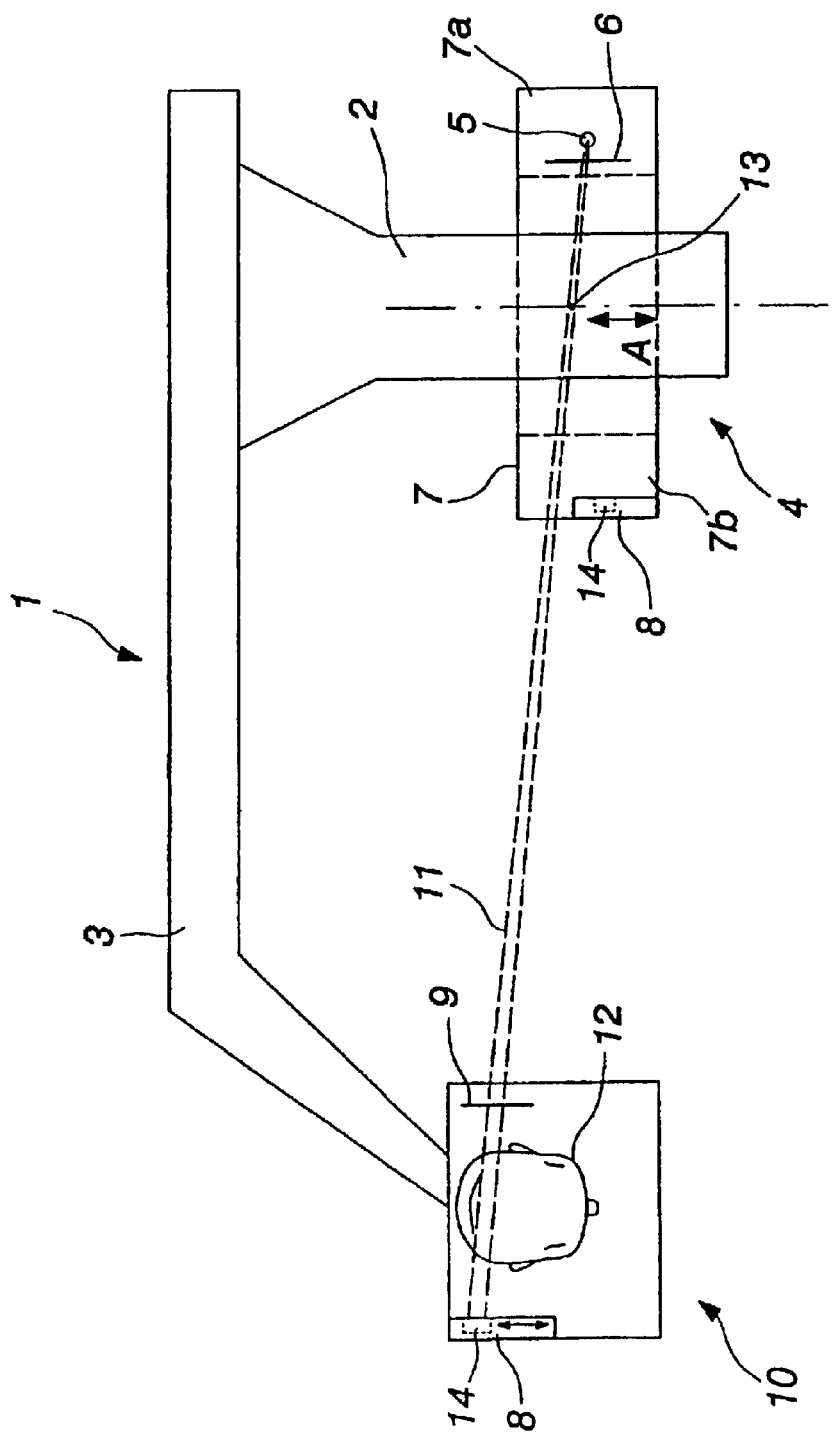
FIG. 1 shows a diagrammatic top view of an apparatus applicable for the method according to the invention.

The apparatus 1 according to FIG. 1 comprises a support part 2, beneath which is connected a panoramic imaging apparatus 4 which turns in a pivoting manner around the rotation centre 13, the imaging apparatus comprising a C arm 7, on one vertical branch 7a of which is arranged an X-ray source 5 and the primary collimator 6 in its vicinity, and on the other branch 7b a line detector camera 8.

Figure 2:
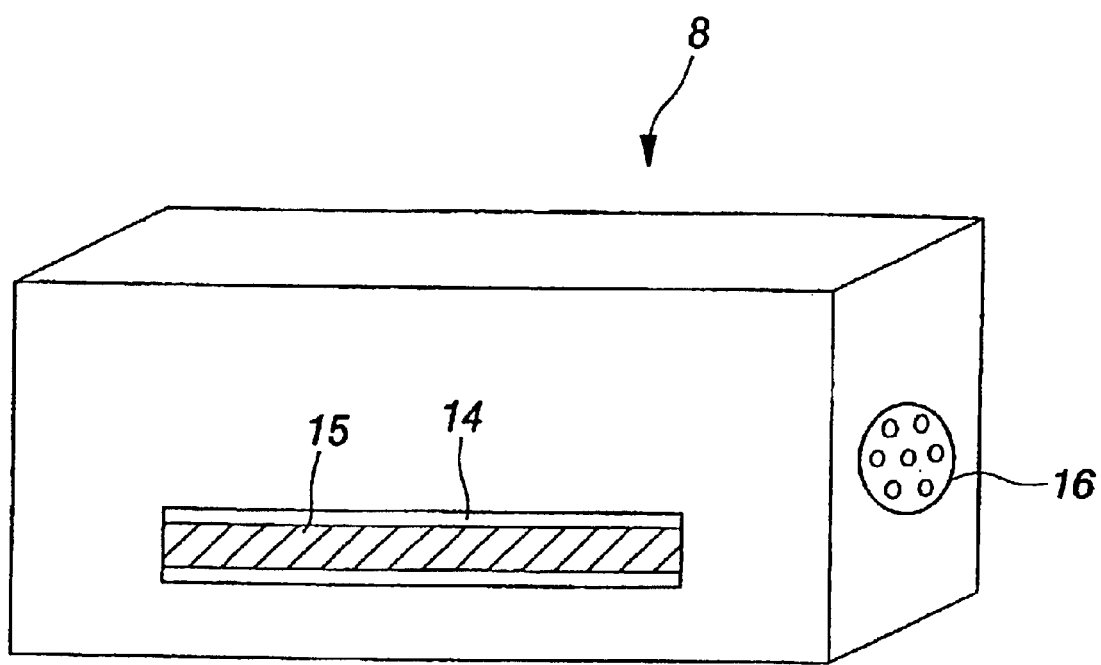
FIG. 2 shows diagrammatically a view in principle of a camera used in the apparatus according to FIG. 1.

FIG. 2 shows diagrammatically one implementation of a line detector camera 8, wherein on one side of the camera is formed a slot 14, behind which, inside the camera 8, is a digital detector 15, for example, a CCD sensor. The panoramic imaging apparatus 4 and its operation are, as such, known to a person skilled in the art. In panoramic imaging, the object to be imaged is placed between the branch parts 7a, 7b of the C arm by means of appropriate guides and supports, after which the X-ray source 5 is switched on and the C arm is rotated about the rotation centre 13, whereby the aperture of the primary collimator 6 is selected in such a way that the ray beam 11, which is substantially on the vertical plane, is directed at the detector 15 behind the substantially vertical slot 14 of the line detector camera 8 on the branch part 7b of the C arm 7, from which detector the image data is transmitted further, for example, to a microprocessor. This process of panoramic imaging will not be described in greater detail in this connection.

To the support part 2 is connected a supporting arm 3, at the other end of which is the cephalometric imaging apparatus 10, which comprises a line detector camera 8 to be placed behind the object being imaged, and a secondary collimator 9 to be placed in front of the object being imaged. In cephalometric imaging, the patient's head is scanned by means of the ray beam 11 from right to left or vice versa. In the apparatus 1 can be used either one joint line detector camera 8, which can be connected to both the panoramic imaging apparatus 4 and the cephalometric imaging apparatus 10 by means of appropriate connection arrangements, or both imaging apparatuses may have separate line detector cameras 8.

In the method according to the invention, the radiation emitted by the X-ray sources 5 is collimated in cephalometric imaging without turning the X-ray source with respect to its support means (branch part 7a of the C arm) in such a way that the ray beam 11 bypasses the position of the line detector camera 8 of the panoramic imaging apparatus 4, whereby, for example, when both imaging apparatuses are equipped with their own line detector cameras, the change from one method of imaging to the other can be done rapidly by selecting the aperture of the primary collimator according to the imaging method. This selection of the primary collimator aperture can be done, for example, by moving the primary collimator 6 manually.

Figure 3:
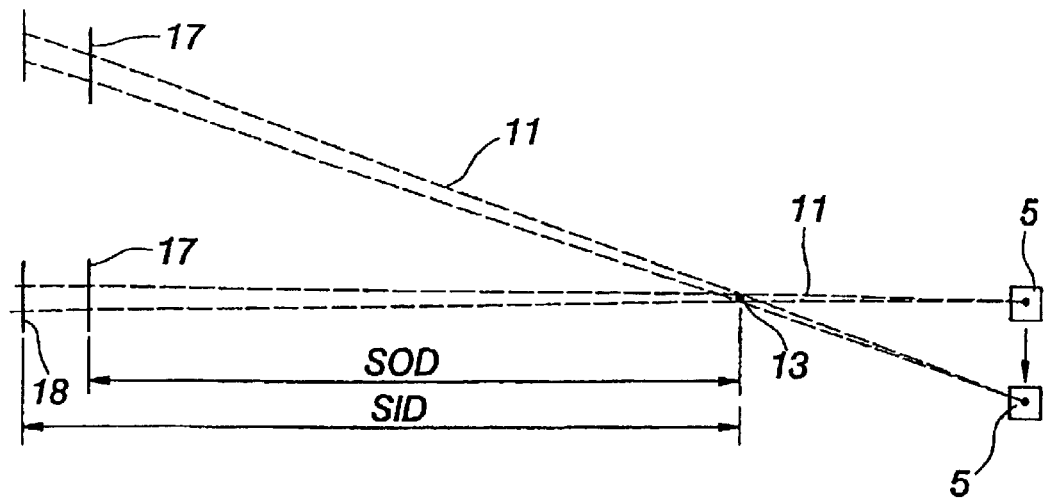
FIG. 3 shows diagrammatically the effect of the rotary movement of the X-ray source on the effective focus.

When cephalometric imaging is carried out by turning the X-ray source 5 about a rotation centre 13 to image the patient's head 12 by means of a vertically positioned ray beam 11, as described, for example, in the publication U.S. Pat. No. 5,511,106, the vertical ratio of enlargement remains the same as without the scanning movement, but the horizontal ratio of enlargement, on the other hand, changes because the rotation centre 13 changes into the effective focal spot instead of the focal spot of the X-ray source 5. FIG. 3 shows a situation where the rotation centre 13 remains in place, in which case, when the X-ray source 5 turns about the rotation centre 13, the X-ray beams 11 travel in each angular position via the rotation centre 13, whereby the rotation centre 13 becomes the effective focal spot for the radiation coming through the object in the layer 17 being imaged on the image plane (detector) 18. In this case, the horizontal ratio of enlargement, which is determined by the ratio of the distance (SID) between the focus and the image plane to the distance (SOD) between the focus and the object, is the ratio of the distance between the rotation centre 13 and the image layer 17 to the distance between the rotation centre 13 and the image plane 18.

Figure 4:
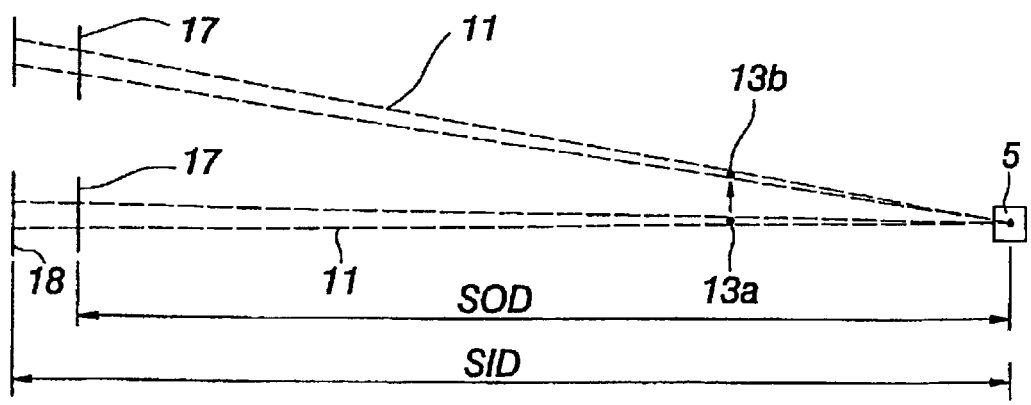
FIG. 4 shows diagrammatically the effect of the transfer of the rotation centre of the rotary movement of the X-ray source on the effective focus.

It is for this reason that, according to the invention, in cephalometric imaging the rotation centre 13 is arranged to be transferred by linear movement transversely with respect to the ray beam 11, as shown by reference marking A in FIG. 1. FIG. 4 shows a situation where the rotation centre has been transferred by linear movement from position 13a to position 13b, whereby the focal spot is transferred to the X-ray source 5, in which case both the horizontal and vertical ratios of enlargement are the same constant in value throughout the entire image field.

What is claimed is:

1. A method for imaging the head area by using a line detector camera (8) equipped with a digital detector, at which line detector camera is directed an X-ray beam (11) through the object being imaged, in which method is used an apparatus (1) which, makes possible the implementation of cephalometric imaging and at least one other imaging method, such as panoramic imaging, which apparatus comprises an X-ray source (5), a primary collimator (6) in conjunction with the X-ray source, at least one line detector camera (8), which is located to a position further away from the X-ray source (5) for implementing cephalometric imaging and/or to a position closer to the said X-ray source for the said other imaging method, end a secondary collimator (9) in the vicinity of the line detector camera (8) intended for cephalometric imaging, characterised in that in the method, the radiation emitted from the X-ray source (5) is collimated in cephalometric imaging in such a way that the ray beam (11) bypasses the position of the line detector camera (8) closer to the X-ray source (5).

2. A method as claimed in claim 1, characterised in that in the method, the collimation is carried out by moving the primary collimator (6) manually.

3. A method as claimed in claim 1, characterized in that in the method, a line detector camera (8) is located both to a position further away from the X-ray source (5) and to a position closer to the X-ray source.

4. A method as claimed is claim 1, characterized in that in the method, a single line detector camera (8) is used alternately both in a position further away from the X-ray source (50) and in position closer to the X-ray source.

5. A method for implementing cephalometric imaging as claimed in claim 1, in which method the X-ray source (5) is arranged to turn about a rotation center (13) situated between the X-ray source and the line detector camera (8), characterized in that in the method, the effective focal spot is transferred from the rotation center (13) to the focal spot of the X-ray source (5) by transferring the rotation center by means of a transverse linear movement (A) with respect to the ray beam (11).

* * * * *